United States Patent
Fan et al.

(10) Patent No.: US 11,928,981 B2
(45) Date of Patent: Mar. 12, 2024

(54) TACTILE VISION

(71) Applicants: Kevin Fan, Sunny Isles Beach, FL (US); Alaa Shamandy, Sunny Isles Beach, FL (US); Spandana Chintapalli, Sunny Isles Beach, FL (US)

(72) Inventors: Kevin Fan, Sunny Isles Beach, FL (US); Alaa Shamandy, Sunny Isles Beach, FL (US); Spandana Chintapalli, Sunny Isles Beach, FL (US)

(*) Notice: Subject to any disclaimer, the term of this patent is extended or adjusted under 35 U.S.C. 154(b) by 0 days.

(21) Appl. No.: 17/846,603

(22) Filed: Jun. 22, 2022

(65) Prior Publication Data
US 2023/0419859 A1    Dec. 28, 2023

(51) Int. Cl.
*G09B 21/00* (2006.01)
*A61F 9/08* (2006.01)

(52) U.S. Cl.
CPC .............. *G09B 21/003* (2013.01); *A61F 9/08* (2013.01)

(58) Field of Classification Search
CPC ................................ G09B 21/003; A61F 9/08
See application file for complete search history.

(56) References Cited

U.S. PATENT DOCUMENTS

| | | | |
|---|---|---|---|
| 9,092,954 B2 | 7/2015 | Visitacion et al. | |
| 2007/0250119 A1 | 10/2007 | Tyler et al. | |
| 2013/0253608 A1 | 9/2013 | Zalevsky et al. | |
| 2015/0296317 A1* | 10/2015 | Park | H04N 23/635 |
| | | | 348/222.1 |
| 2019/0332167 A1 | 10/2019 | Chenegros et al. | |
| 2019/0332175 A1* | 10/2019 | Väänänen | G06V 20/20 |
| 2020/0004291 A1* | 1/2020 | Wexler | G10L 15/10 |

FOREIGN PATENT DOCUMENTS

| | | |
|---|---|---|
| WO | WO 2013/018090 A1 | 2/2013 |
| WO | WO2015159237 A1 | 10/2015 |
| WO | WO2018204745 A1 | 11/2018 |

OTHER PUBLICATIONS

Troy McDaniels et al., Using a Haptic Belt to Convey Non-Verbal Communication Cues During Social Interactions toIndividuals Who Are Blind, IEEE International Workshop on Haptic Audio Visual Environments and Game Processing (2008), https://asu.pure.elsevier.com/en/publications/using-a-haptic-belt-to-convey-non-verbal-communication-cues-durin-2.

(Continued)

*Primary Examiner* — Kathleen V Nguyen
(74) *Attorney, Agent, or Firm* — IPEC/MIPLRC

(57) ABSTRACT

A seeing device and process that enables a visually impaired user to "see" using touch. It comprises: Sensors/cameras worn approximately at eye level, a microprocessor, and a garment that contains small tactile elements in a matrix that vibrate in a pattern related to the location of objects in front of the user. The cameras take pictures of the area and then map the depth and position of objects. This map is translated onto a person's skin through the garment with tactile elements with each tactile element corresponding to a zone in real space. Some of the tactile elements will trigger sequentially in a snaking pattern with only certain ones activating in a pattern. This will help the person sense where there are objects in his/her path.

19 Claims, 3 Drawing Sheets

(56) References Cited

OTHER PUBLICATIONS

Rebekka Hoffman et al., Evaluation of an Audio-Haptic Sensory Substitution Device for Enhancing Spatial Awareness for the Visually Impaired, Optom Vis. Sci. (2018), https://www.ncbi.nlm.nih.gov/pmc/articles/PMC6133230/pdf/opx-95-757.pdf.
Paul Bach-y-Rita et al., Vision Substitution by Tactile Image Projection, Nature (Mar. 8, 1969), https://www.nature.com/articles/221963a0.pdf.
Ramiro Valazquez, Wearable Assistive Devices for the Blind, Springer (2010), https://arxiv.org/ftp/arxiv/papers/1611/1611.09480.pdf.

* cited by examiner

TACTILE VISION

BACKGROUND OF THE INVENTION

Field of the Invention

The present invention relates to a device to help a visually impaired user navigate using sensory substitution technology.

Background Art

According to the National Institutes of Health, one million Americans, and according to World Health Organization, forty million people worldwide are legally blind. While there are many services to help the blind retain function and autonomy, they are never fully independent.

Currently, to help navigate life visually impaired people use aids such as white canes, braille, guide dogs, voice-controlled devices, and human assistance. Recently there has been interest in finding more hands-free devices to help visually impaired people navigate an area and spatially orient themselves to objects around them. Some work has been done to develop an implantable artificial retina, but so far none have been successful. Regardless, any such devices will cost tens, if not hundreds, of thousands of dollars per patient to implement and will require invasive surgery.

BRIEF DESCRIPTION OF THE DRAWINGS/FIGURES

The accompanying drawings, which are included to provide a further understanding of the disclosed subject matter, are incorporated in and constitute a part of this specification. The drawings also illustrate embodiments of the disclosed subject matter, and together with the detailed description below, serve to explain the principles of embodiment of the disclosed subject matter. No attempt is made to show structural details in more detail than may be necessary for a fundamental understanding of the disclosed subject matter and various ways in which it may be practiced.

Further embodiments, features, and advantages of the present invention, as well as the operation of the various embodiments of the present invention, are described below with reference to the accompanying drawings.

DETAILED DESCRIPTION OF THE INVENTION

A preferred embodiment of the present invention is now described with reference to the figures. While specific configurations and arrangements are discussed, it should be understood that this is done for illustrative purposes only. A person skilled in the relevant art will recognize that other configurations and arrangements can be used without departing from the spirit and scope of the invention. It will be apparent to a person skilled in the relevant art that this invention can also be employed in a variety of other systems and applications.

The present invention represents a low-cost, totally non-invasive "retina" that can allow a visually impaired individual to navigate an environment, interact with important environmental features, and/or find personal belongings. This device is a visual prosthetic device. The device uses haptic feedback to help a user locate objects around them. The user can then learn to navigate and make decisions based on the location of objects.

Figure 1:
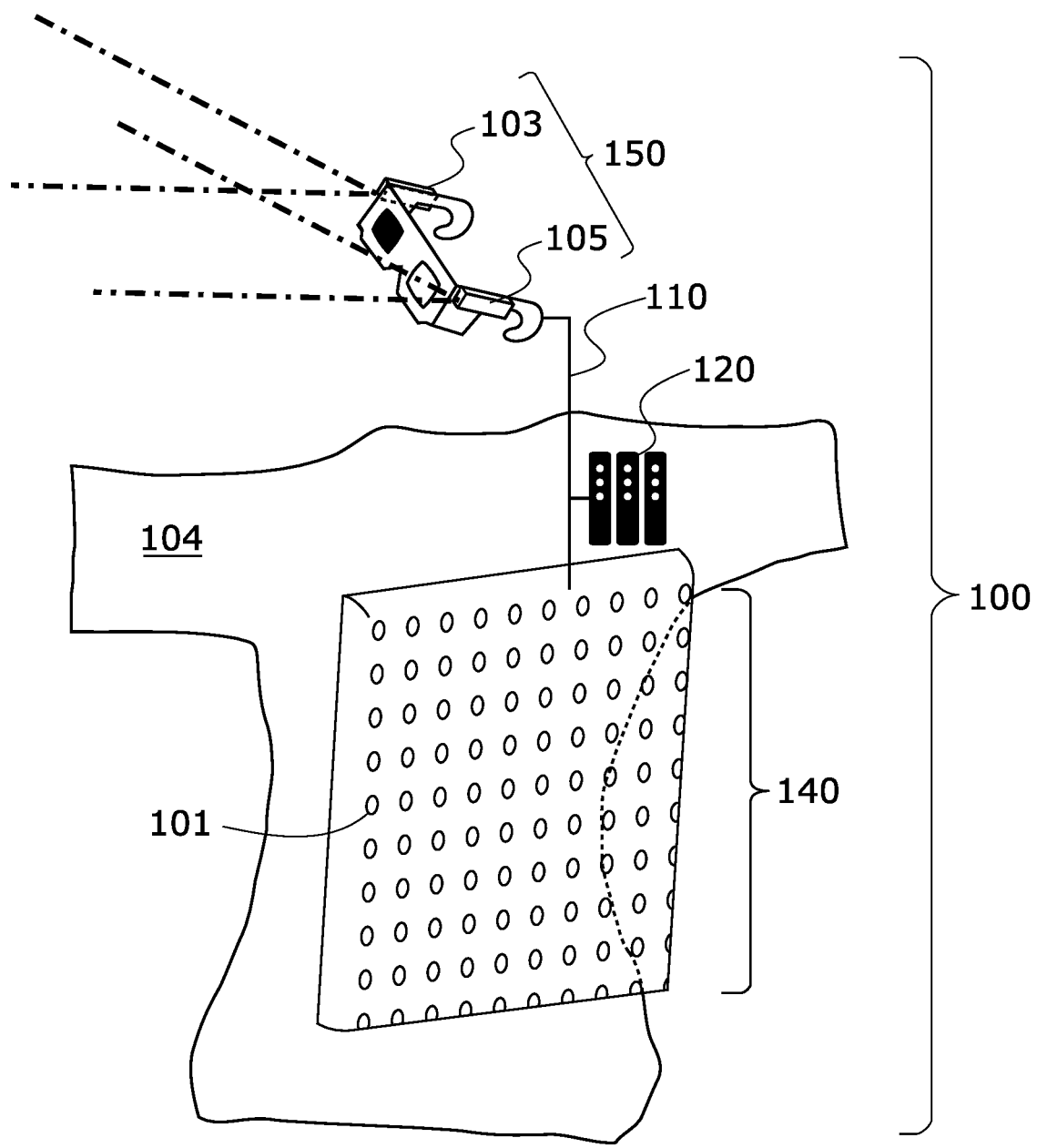
FIG. 1 is an overview depicting an embodiment of the different components of the device.

FIG. 1 illustrates an embodiment of the device, 100. The device comprises in one embodiment a garment 104, such as a shirt or vest, with a matrix 140 of tactile devices 101; a sensor system 150 consisting of multiple sensors, which in this embodiment are labeled 103 and 105, that may be mounted at head level; and a microprocessor 120 that interfaces with the matrix 140 and sensors 103 and 105. In one embodiment, the garment 104 is a shirt made of nylon or other fabric. In another embodiment, the garment 104 is a vest. The matrix 140 can be attached to or embedded in the garment 104. In one embodiment, the matrix 140 is placed on the front side of the garment 104, and in another embodiment the matrix 140 is placed on the back side of the garment, in another embodiment, the matrix 140 is embedded throughout the entire garment. Power for the tactile devices, the sensor system, the tactile devices, and the microprocessor may be supplied by a portable power source, such as a battery or battery pack. In an embodiment, such a power source may be rechargeable. In an embodiment, any of the above components may be separately removed and replaced for maintenance.

In one embodiment, the tactile devices 101 vibrate when activated. In another embodiment, the tactile devices 101 deliver pressure (e.g., a light pin prick or touch) to the user when activated. In other embodiments, the tactile devices 101 may deliver localized heat (thermomodulation) or an electrical discharge to the user when activated.

In one embodiment, the sensors 103 and 105 are mounted on, embodied in, or designed to look like a pair of glasses 150 that the user wears. In other embodiments, the sensors 103 and 105 are mounted in, embodied in, or designed to resemble a headband, sweat band, or hat that the user wears. In one embodiment, the sensor 103 is a light sensing camera that recognizes objects and the sensor 105 is an IR depth sensor that determines the depth of each object. In another embodiment, both sensors 103 and 105 are light sensing cameras that recognize objects and the binocular disparity between the two sensors and are used to calculate depth. In an alternative embodiment, the sensor system may emit acoustic (sound) waves and capture returning acoustic waves to determine depth and location of the objects. In one embodiment, the sensors 103 and 105, microprocessor 120, and garment 100 are all connected by one or more cables, such as cable 110. In another embodiment, the sensors 103 and 105, microprocessor 120, and garment 100 are connected wirelessly.

The sensors 103 and 105 scan the area of interest and, with microprocessor 120, create a representation or map of what is in that area. Such a map or representation may take the form of an array or other data structure and will be discussed below with respect to FIG. 3. The microprocessor 120 takes the information captured by the two sensors 103 and 105 and combines them to determine a depth coordinate and direction coordinate of an obstacle in front of the user, where depth refers to an approximate distance from the user. The microprocessor 120 may represent computational means for determining a coordinate position. Each possible pair of coordinates corresponds to specific tactile devices 101. If there is an obstacle or object (as appears in FIG. 3)

in a location (i.e., at a depth and direction) that corresponds to a specific tactile device 101, then the corresponding tactile device 101 will activate. This informs the user that an object is present at a location defined by those coordinates.

Figure 2:
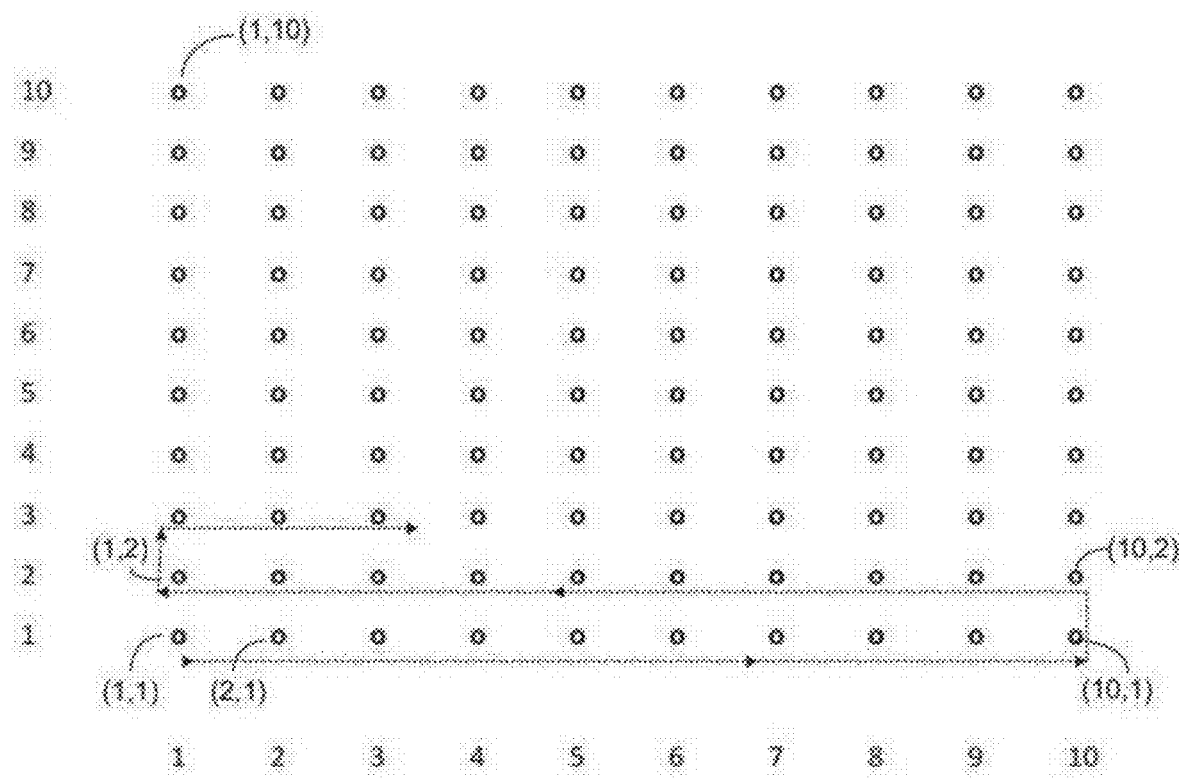
FIG. 2 is a depiction of a matrix showing the order and direction in which the tactile elements can activate, according to an embodiment.

FIG. 2 shows a functional view of the two-dimensional matrix 140 of tactile devices 101. Each of the tactile devices 101 may be identified by a two-dimensional (x, y) coordinate using conventional Cartesian notation. The device in the second column and in the first (lowest) row would be identified as (2, 1) as shown, for example. In one embodiment the matrix 140 is 10×10 and contains 100 tactile devices 101. Other embodiments may have different sized matrices. In one embodiment the sensors 103 and 105 will have a range of approximately 10 feet. Each first coordinate may correspond to the horizontal position of the detected object 401, e.g., the direction of the object in a left-to-right scan, and each second coordinate may correspond to the depth of (or distance to) the object in that direction. Potential activation of a tactile device may start at position (1, 1) and if the sensors 103 and 105 detect an object at the depth and direction corresponding to the tactile device at (1, 1) then that tactile device will briefly activate. In an embodiment, this activation will last for 0.1 second. As discussed above, this activation may result in a vibration or other event felt by the user at the spot of the tactile device at (1, 1). If the sensors 103 and 105 do not detect an object 401 at the spatial location corresponding to tactile device at (1, 1), then this tactile device will not activate. The system will then consider the next position, corresponding to the tactile device at (2, 1). In the example discussed here, this next position may be slightly to the right of the previous position and at the same depth. The tactile device at (2, 1) will either activate or not activate as it did with the previous coordinate. The potential activations of tactile devices may, in an embodiment, move in a snaking pattern starting at (1, 1) as shown in FIG. 2. This progression may continue until it reaches the last tactile device at (1, 10). At each position, the tactile device 101 at that position will activate or not activate, depending on whether an object is detected at a corresponding spatial location.

The positions of objects (and of the user) may change over time if the user or objects move or appear. The process may therefore repeat over time to give a live action sense of the environment being captured. The sensors 103 and 105 may determine new locations of objects relative to the user, and the process may be restarted at position (1, 1).

The above process is facilitated by use of "smart" devices (detailed in next paragraph) to locate the objects at any given moment. When an image is captured, objects may be recognized and labeled using image recognition software. Objects are located using either binocular disparity or a depth sensor as described above. Each object is given a (x, y) coordinate based on its location, all the objects are plotted on a "birds-eye, top down" view of the environment, and finally the tactile devices in the matrix are activated sequentially at a predetermined number of frames per second. A K×K' matrix is used, where the entry location (x, y) of the matrix holds a binary value representing the presence or absence of an object at direction x and a distance (or depth) y. If the information transferred indicates that a scan detected an object at (x, y), the array's value at that location will be read and the tactile device will activate at the corresponding position and appropriate moment in the progression of activations. In an embodiment, characteristics of objects such as height, shape, color, type are represented by the tactile device by use of different patterns of tactile stimulus or by modulating amplitude of tactile stimulation. For example the intensity, frequency, or type of tactile stimulus may be varied according to objects' characteristics.

The information retrieved from the surrounding environment may be obtained by different types of sensors. In one embodiment, binocular vision is achieved using a dual-camera. In other embodiments, the same objective is achieved using a camera with depth sensors, telephoto lens or other types of sensors. In future embodiments, speakers, bone conduction or headphones may be used to achieve auditory modalities. Computer vision may be used to locate, identify and separate objects in a field of view, and to determine the character, identity, or class of the objects. The computer vision functionality may be implemented at least in part as software that is executable on microprocessor 120.

Figure 3:
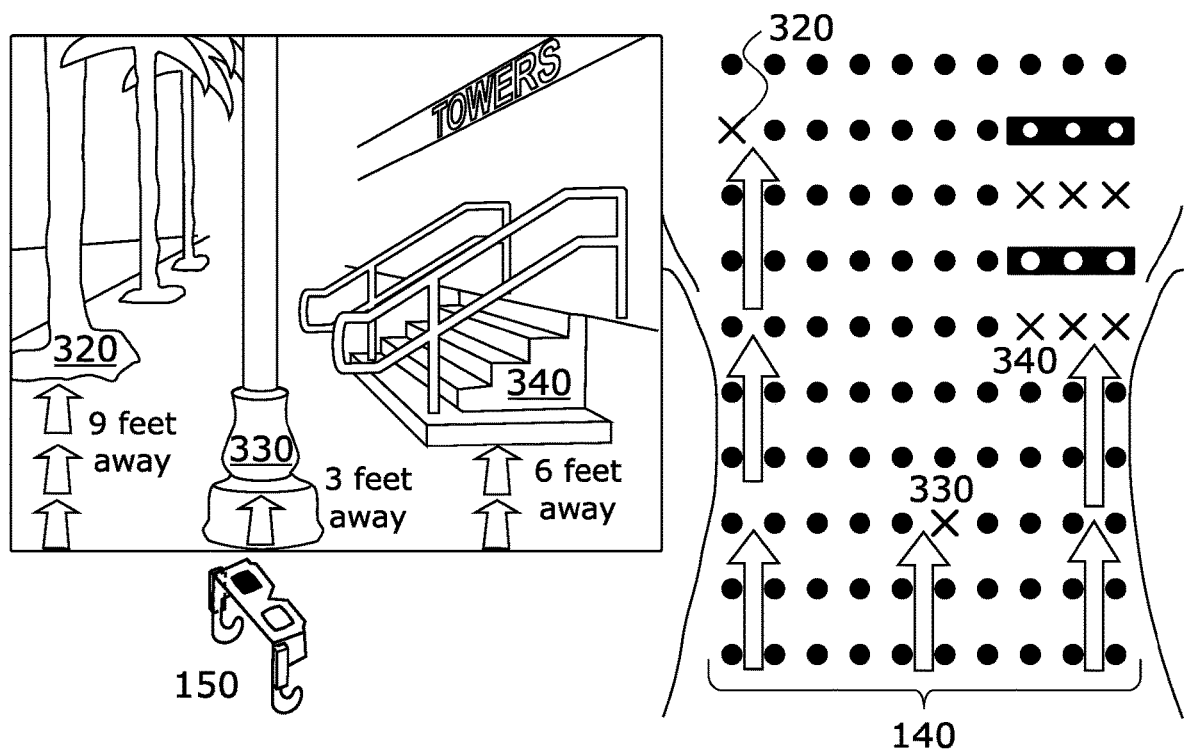
FIG. 3 is a diagram showing an example scenario, according to an embodiment.

An example matrix is shown in FIG. 3 along with its use in an example scenario. A user may be equipped with the device 100 of FIG. 1. The sensor system 150 worn by the user may detect three objects 320, 330, and 340 in this example. Object 320 may lie in a horizontal position 1 (e.g., at a leftmost direction in the field) and be at a distance of nine feet away. As a result, the microprocessor may write a value of true ("t") at location (1, 9) of array 140. Analogously, object 330 may lie at direction 5 (nearly straight ahead) and a distance of three feet away. The microprocessor may thus write a value of true at location (5, 3) of array 140, i.e., the $5^{th}$ column and 318 row of array 140. Object 340 may lie in direction 7 and at a distance of six feet away. The microprocessor may thus write a value of true at location (7, 6) of array 140. Since no other objects are present, the remaining elements of the array 140 may be empty or hold a value of false (not shown) by default.

Given the array 140 as shown, the process described with respect to FIG. 2 may then take place. In an embodiment, the data in array 140 may be read element-by-element in a snake pattern as shown, starting at (1, 1). When a true value is found in a given element (x, y), a corresponding tactile device (x, y) may be activated. In such an embodiment, the appropriate tactile devices will activate following a snake pattern following the pattern shown in array 140.

In the above description, the processing may be performed by microprocessor 120. In an alternative embodiment, the processing may be performed externally at least in part. In such an embodiment, system 100 may be connected to a data network such as the Internet, and the required computation may be performed partially or completely by a remote computing system. In such an embodiment, information received through sensors 103 and 105 may be sent wirelessly to such a remote computing system, which would then return data sufficient to activate the appropriate tactile device(s) 101. In such an embodiment, system 100 would also include a communications module (not shown) adapted for the necessary communications with the network, e.g., the Internet. Further, the remote computing functionality may be implemented at least in part on a mobile computing device (e.g., a smart phone) running a third party mobile application.

Moreover, the use of a remote computing system may allow for use of a larger external database of known objects to facilitate the computer vision functionality described above.

The foregoing description, for purposes of explanation, has been described with references to specific embodiments. However, the illustrative discussions above are not intended to be exhaustive or to limit embodiments of the disclosed subject matter to the precise forms disclosed. Many modifications and variations are possible in view of the above teachings. The embodiments were chosen and described in order to explain the principles of embodiments of the disclosed subject matter and their practical applications to thereby enable others skilled in the art to utilize those embodiments as well as various embodiments with various modifications as may be suited to the particular use contemplated.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventors, and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

What is claimed is:

1. A wearable device, comprising:
   a sensor system for collecting information about a user's environment;
   a computational means, in communication with the sensor system, for determining coordinate positions, relative to the user, of one or more objects in the environment;
   computer vision software, executable on the computational means, to determine character, identity, or class of the objects in the environment;
   a plurality of tactile stimulation elements that are contained within or attached to a garment configured to be worn by the user and that interface with the user's skin and are configured to be activated in a snaking pattern such that information about the coordinate positions and character of each of the one or more objects is communicated to the user;
   a communications module connecting the sensor system and the tactile stimulation elements to a network; and
   a portable power source configured to power the sensor system, the computational means, and the tactile stimulation elements.

2. The wearable device of claim 1 wherein said sensor system contains at least one camera.

3. The wearable device of claim 2 wherein said sensor system uses binocular disparity, and is configured to permit determination of the distance of each object in the environment relative to the user.

4. The wearable device of claim 1 wherein said sensor system contains a depth sensor configured to permit determination of the distance of each object in the environment relative to the user.

5. The wearable device of claim 4 wherein said depth sensor uses infrared radiation.

6. The wearable device of claim 4 wherein said depth sensor uses sound waves.

7. The wearable device of claim 1 wherein said sensor system is worn on the head.

8. The wearable device of claim 7 wherein said sensor system is designed to look like eyeglasses.

9. The wearable device of claim 7 wherein said sensor system is designed to look like a headband.

10. The wearable device of claim 7 wherein said sensor system is designed to look like a hat.

11. The wearable device of claim 1 wherein the communications module allows for communication with pre-existing third-party mobile applications.

12. The wearable device of claim 1 wherein additional computer vision software is executed on a remote computing system that is configured to access an external database of known objects.

13. The wearable device of claim 1 wherein activation of said tactile stimulation elements stimulates the skin via one or more of vibration, electrical discharge, thermomodulation, and pressure.

14. The wearable device of claim 13 wherein information about the character of any object can be communicated by modulating the intensity, frequency, or type of tactile stimulus.

15. The wearable device of claim 1 wherein the sensor system, computational means, and tactile sensors are configured to communicate wirelessly.

16. The wearable device of claim 1 wherein the sensor system, computational means, and tactile sensors can be separately replaced.

17. The wearable device of claim 1 wherein said tactile stimulation elements stimulate the skin via electrical discharge.

18. The wearable device of claim 17 wherein information about the character of any object can be communicated by modulating frequency of tactile stimulus.

19. The wearable device of claim 17 wherein information about the character of any object can be communicated by modulating the intensity of tactile stimulus.

* * * * *